US010350314B2

(12) United States Patent
Kvaale et al.

(10) Patent No.: US 10,350,314 B2
(45) Date of Patent: Jul. 16, 2019

(54) PREPARATION OF COMPOSITION COMPRISING GAS MICROBUBBLES

(71) Applicant: GE Healthcare AS, Oslo (NO)

(72) Inventors: Svein Kvaale, Oslo (NO); Ole Johannes Tokerud, Oslo (NO)

(73) Assignee: GE HEALTHCARE AS, Oslo (NO)

(*) Notice: Subject to any disclaimer, the term of this patent is extended or adjusted under 35 U.S.C. 154(b) by 1 day.

(21) Appl. No.: 14/579,905

(22) PCT Filed: Jun. 25, 2013

(86) PCT No.: PCT/EP2013/063218
§ 371 (c)(1),
(2) Date: Dec. 22, 2014

(87) PCT Pub. No.: WO2014/001297
PCT Pub. Date: Jan. 3, 2014

(65) Prior Publication Data
US 2015/0250904 A1 Sep. 10, 2015

(30) Foreign Application Priority Data

Jun. 26, 2012 (EP) .................................. 12173606

(51) Int. Cl.
A61K 49/22 (2006.01)
B01J 13/02 (2006.01)
B01J 19/24 (2006.01)

(52) U.S. Cl.
CPC ............ *A61K 49/223* (2013.01); *B01J 13/02* (2013.01); *B01J 19/248* (2013.01); *B01J 2219/00076* (2013.01); *B01J 2219/24* (2013.01)

(58) Field of Classification Search
None
See application file for complete search history.

(56) References Cited

U.S. PATENT DOCUMENTS

| 4,957,656 | A |   | 9/1990 | Cerny et al. |
|-----------|---|---|--------|--------------|
| 5,370,955 | A |   | 12/1994 | Toth et al. |
| 5,552,133 | A |   | 9/1996 | Lambert et al. |
| 5,730,955 | A | * | 3/1998 | Lohrmann ........... A61K 49/223 424/9.52 |
| 5,855,865 | A | * | 1/1999 | Lambert ................ B01J 13/02 424/9.52 |
| 5,976,501 | A |   | 11/1999 | Joblonski |
| 7,866,378 | B2 |  | 1/2011 | Nakamura et al. |
| 2006/0093614 | A1 | | 5/2006 | Nakamura et al. |
| 2008/0063603 | A1 | | 3/2008 | Schneider et al. |
| 2012/0037232 | A1 | * | 2/2012 | Shen ................... B01F 11/0266 137/1 |

FOREIGN PATENT DOCUMENTS

| AU | 722742 B2 | 8/2000 |
|----|-----------|--------|
| DE | 10 2005 020727 A1 | 11/2006 |
| EP | 0359246 | 3/1990 |
| EP | 0633030 A1 | 1/1995 |
| EP | 0633030 B1 | 4/1999 |
| EP | 2864033 B1 | 4/2016 |
| JP | 2-115037 A | 4/1990 |
| JP | 07047251 A | 2/1995 |
| JP | 8-509002 A | 9/1996 |
| JP | 2000084383 A | 3/2000 |
| JP | 2000512281 A | 9/2000 |
| JP | 2006-162238 A | 6/2006 |
| RU | 2147226 C1 | 4/2000 |
| WO | 1993/005819 A1 | 4/1993 |
| WO | 1995/001187 A1 | 1/1995 |
| WO | 1997/029783 A1 | 8/1997 |
| WO | 2014/001297 A2 | 1/2014 |
| WO | 2010/115377 A1 | 10/2014 |

OTHER PUBLICATIONS

International Preliminary Report on Patentability received for PCT Patent Application No. PCT/EP20131063218, completed on Feb. 11, 2015, 12 pages.
International Search Report and Written Opinion received for PCT Patent Appliation No. PCT/EP2013/063218, dated Aug. 1, 2014, 16 pages.
Office Action and Search Report received for Russian Patent Application No. 2014150473, dated Apr. 27, 2017, 12 pages (5 pages of English Translation + 7 pages of Official Copy).
Office Action Received for Japanese Patent Application No. 2015-519044, dated May 9, 2017, 4 pages (Official Copy only).
India Examination Report corresponding to Indian Application No. 10714/DELNP/2014, dated Aug. 28, 2018.
Japanese Office Action corresponding to JP Application No. 2015-519044, dated Sep. 18, 2018.

* cited by examiner

*Primary Examiner* — Michael G. Hartley
*Assistant Examiner* — Jennifer Lamberski
(74) *Attorney, Agent, or Firm* — Arent Fox, LLP

(57) ABSTRACT

A process for preparing a composition comprising encapsulated gas microbubbles, the process comprising: providing an aqueous protein solution of a heat-denaturable protein at a temperature necessary to achieve incipient denaturation; heating a gas by using heat from the heated protein solution; mixing the heated gas and the heated protein solution to obtain a gas/liquid mixture; and dispersing the gas into the protein solution by subjecting the gas/liquid mixture to mechanical shear forces to form a composition of gas microbubbles encapsulated by denatured protein.

11 Claims, 5 Drawing Sheets

PREPARATION OF COMPOSITION COMPRISING GAS MICROBUBBLES

CROSS-REFERENCE TO RELATED APPLICATIONS

This is a national stage application under 35 U.S.C. § 371 of prior-filed, co-pending, PCT application serial number PCT/EP2013/063218, filed on Jun. 25, 2013, which claims priority to EP patent application serial number 12173606.0, filed on Jun. 26, 2012, both of which are incorporated by reference herein in their entireties.

FIELD OF THE INVENTION

Embodiments of the present invention relate to ultrasound contrast media. More particularly, embodiments relate to a process for preparation of ultrasound contrast media, particularly to compositions comprising gas microbubbles and more particularly to microbubbles encapsulated by proteins prepared using mechanical energy.

BACKGROUND TO THE INVENTION

It is well known that ultrasonic imaging comprises a valuable diagnostic tool, for example in studies of the vascular system, particularly in cardiography, and of tissue microvasculature. A variety of ultrasound contrast media has been proposed to enhance the acoustic images so obtained, including suspensions of solid particles, emulsified liquid droplets, gas bubbles and encapsulated gases or liquids. The most successful ultrasound contrast media have generally consisted of dispersions of small bubbles of gas that can be injected intravenously. For example WO 97/29783 and WO93/05819 describe such microbubble dispersions. If appropriately stabilised, microbubbles may permit highly effective ultrasound visualisation of, for example, the vascular system and tissue microvasculature, often at advantageously low doses. Such contrast media typically include a material stabilising the gas, for example emulsifiers, oils, thickeners or sugars, or by entraining or encapsulating the gas in a variety of systems, e.g. as porous gas-containing microparticles or as encapsulated gas microbubbles. The microbubbles include a gas that is essential for the performance of the ultrasound contrast agent, and a variety of gases have been found to enhance properties such as the microbubble stability and duration of echogenic effect. One group of ultrasound contrast media is prepared and delivered as a ready-made preparation comprising a liquid composition of encapsulated gas microbubbles.

Various processes can be used to prepare microbubbles. Such gas-containing microbubbles may be produced by shaking or sonicating a liquid containing a membrane-forming material in the presence of a suitable gas or gas mixture. Other processes include spray drying. However, the microbubbles produced by such techniques have a broad size distribution which may vary from batch to batch and moreover the yield, i.e. the percentage of membrane forming material which ends up in appropriately sized microbubbles, may also vary from batch to batch. U.S. Pat. No. 5,552,133 describes a process for making encapsulated gas microspheres comprising a heat-denaturable protein encapsulating a gas, using a colloid mill. An aqueous solution of a heat-denaturable protein is combined with a gas, and is mixed by applying mechanical shear forces to the mixture to form a suspension of gas microbubbles, wherein the protein becomes denatured and deposited at the gas-solution interface.

When preparing microbubbles it is important to have a robust process that repeatedly provides a product according to product specifications. Desirably the microbubbles produced will have a narrow size distribution about the desired microbubble size, generally 1 to 7 µm, e.g. 3-5 µm. Desirable, the percentage of large microbubbles, such as above 7 µm should be minimal and well limited. To achieve this, the standard deviation of the microbubble sizes should be small. This has not been achieved when using the processes of the prior art. One challenge is to produce reproducible microbubbles having a narrow size distribution throughout the process cycle and each time the process is run. A robust process for preparing contrast media, such as for preparing a composition comprising gas microbubbles encapsulated by a denatured protein, has been sought.

SUMMARY OF THE INVENTION

In view of the needs of the art, embodiments of the present invention provide a robust process for preparing a contrast media, such as for preparing a composition comprising gas microbubbles encapsulated by a denatured protein. A process has now been identified and developed wherein the yield can be improved and undue production of oversized and undersized microbubbles is avoided. In the process of an embodiment of the invention, an aqueous solution of a heat-denaturable protein is combined with a gas, and these are mixed mechanically using high shear forces. Surprisingly it has been found that before mixing the protein and the gas, both the protein and the gas should be heated, providing a robust process wherein the generated microbubbles have a narrow size distribution.

Accordingly, in a first aspect, the present invention provides a process for preparing a composition comprising encapsulated gas microbubbles, comprising:
  i) providing an aqueous protein solution of a heat-denaturable protein at a temperature necessary to achieve incipient denaturation;
  ii) heating a gas by using heat from the heated protein solution;
  iii) mixing the heated gas and the heated protein solution to obtain a gas/liquid mixture;
  iv) dispersing the gas into the protein solution by subjecting the gas/liquid mixture to mechanical shear forces to form a composition of gas microbubbles encapsulated by denatured protein.

In a second aspect, the present invention provides a feeding pipe useful in the preparation of a composition comprising encapsulated gas microbubbles, wherein the feeding pipe comprises
  i) a first inlet and a second inlet providing the respective openings of two paths,
  ii) a heat transferring section comprising a longitudinal wall separating the two paths,
  iii) one outlet connectable to an inlet of a mixing device.

In a third aspect, the present invention provides an apparatus comprising the feeding pipe of the present invention. The apparatus according to this aspect may comprise:
  i) a mixing device generating high mechanical shear forces, and having an inlet and an outlet;
  ii) a feeding pipe comprising a first inlet and a second inlet providing the respective openings of two paths, a heat transferring section comprising a longitudinal wall separating the two paths, and one outlet connected to the inlet of the mixing device;

iii) a feeding tank for a liquid composition connected to the first inlet of the feeding pipe;

iv) a gas tank connected to the second inlet of the feeding pipe.

BRIEF DESCRIPTION OF THE FIGURES

Further aspects, advantages and features of the invention can be derived from the following detailed description of exemplary embodiments of the invention, with reference to the drawings.

DETAILED DESCRIPTION OF THE INVENTION

Figure 1:
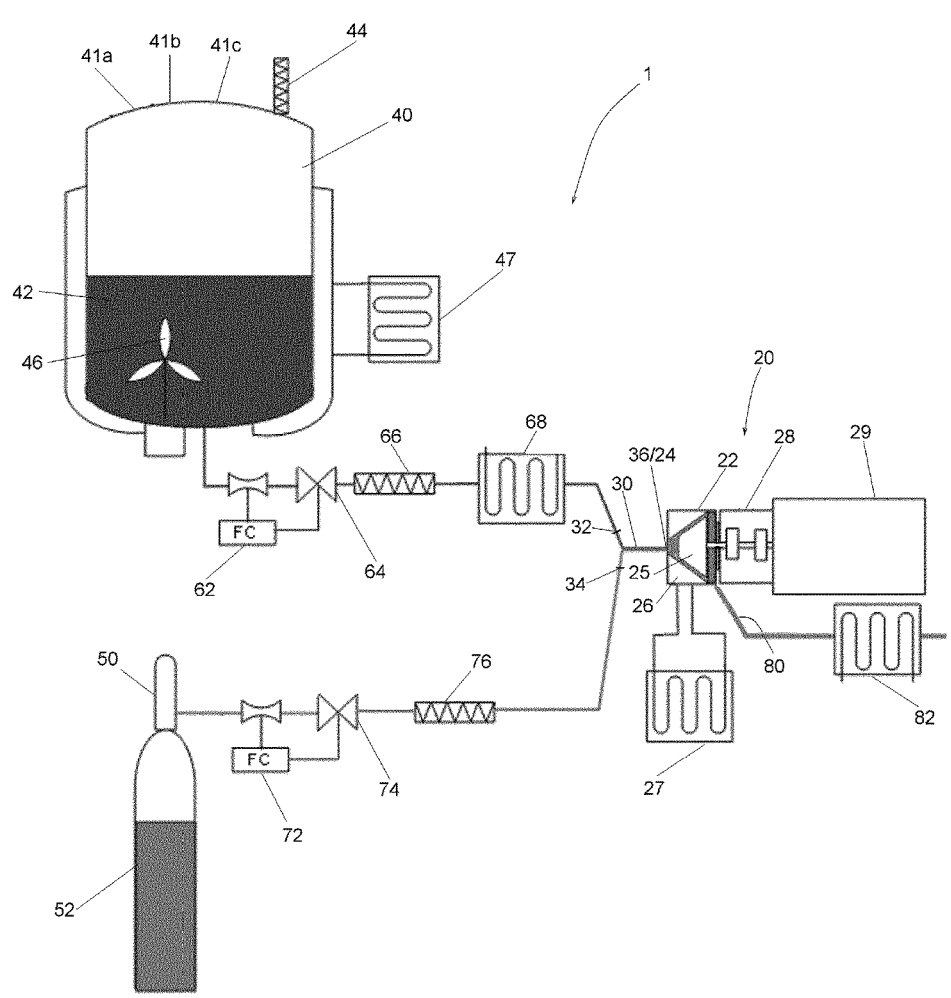
FIG. 1 schematically shows an apparatus useful in the preparation of a composition comprising gas microbubbles encapsulated by a denatured protein according to an embodiment of the invention.

In a first aspect the invention provides a process for preparing a composition comprising encapsulated gas microbubbles, comprising:

i) providing an aqueous protein solution of a heat-denaturable protein at a temperature necessary to achieve incipient denaturation;

ii) heating a gas by using heat from the heated protein solution;

iii) mixing the heated gas and the heated protein solution to obtain a gas/liquid mixture;

iv) dispersing the gas into the protein solution by subjecting the gas/liquid mixture to mechanical shear forces to form a composition of gas microbubbles encapsulated by denatured protein.

Using the process of some embodiments of the invention, heating both the protein solution and the gas prior to entering the mixing device used in step iv), it is avoided that the gas expands when this is fed into the mixing device. This has been found to be a key factor in providing a stable process and microbubbles of a narrow size distribution. The process uses heat from the protein solution to heat the gas, before these are combined. Hence, both the protein solution and the gas to be encapsulated are preheated prior to being introduced into the mixing device. The protein is heated to the temperature where incipient denaturation of the protein occurs. The denaturation temperature is the temperature at which insoluble material is first observed. The denaturation temperature can be obtained from tables of thermal protein denaturation in the literature, or experimentally by any known method. The denaturation temperature of the protein in solution will normally be in the range of 50-100° C., varying for different proteins, purity and source etc. In the process of some embodiments of the invention, albumin is a protein for providing encapsulated microbubbles. When using an albumin solution this is heated to 60-80° C., particularly to 65-75° C. and more particularly to 68-72° C. The exact temperature needed depends on several parameters, and it should also be taken into consideration that the temperature may slightly increase when the gas/protein solution mixture has entered into the mixing device as a result of being exposed to mechanical energy. When the components are entering into the mixing device heat has been transferred from the protein solution to the gas ensuring that the gas has a temperature that is close to the temperature in the mixing device, such that the gas does not expand significantly when entering the mixing device. The gas should hence be heated to a temperature close to the temperature of the heated protein, such as to at least a temperature of the denaturation temperature minus 20° C., particularly to the denaturation temperature minus 15° C., and more particularly to the denaturation temperature minus 10° C. The protein solution and the gas may have about the same temperature when entering the mixing device. The protein is heated e.g. by using a heat exchanger. The transfer of heat from the protein solution to the gas can be achieved by transporting the gas and the heated protein in paths in close proximity with each other and going in parallel before the two separated streams are combined and entered into the mixing device. Hence, heat is transferred from the protein solution to the gas stream through heat-conducting walls separating the different paths of a pipe.

In a further embodiment of the invention the mixture of the heated gas and the heated protein solution takes place at, or very nearby, the inlet of the mixing device. Hence, the gas and the protein solution are premixed right before the dispersing step takes place. It has been found that if the gas and the protein solution are combined at a long distance from the inlet of the mixing device a plug flow is generated and this creates variation in the size distribution of the microbubbles produced. When combining the two components at the inlet of the mixing device a much better control of the mixing process is achieved. The protein solution and the gas are hence combined just before or at the entering of the mixing device. This is achieved by transporting the protein solution and the gas in paths that are in close contact with each other and which are going in parallel before the two heated streams are combined near the entrance of the mixing device. By doing this, the gas stream and the protein solution stream will enter the mixing device as one evenly distributed uniform mixture, without any plug flow, and this is then subjected to mechanical mixing producing the microbubbles. As the manufacturing of the bubbles in the mixing device, such as in a mill, goes very quickly, it has been found important that the gas and the encapsulating protein are evenly distributed, having a stabile concentration throughout a production cycle, when entering the mixing device.

Further, rather than pumping the protein solution, e.g. by using a peristaltic pump, into the mixing apparatus, it has been found that providing the protein solution under a steady feeding pressure, e.g. combined with a control valve controlling the flow rate, affects the size distribution of the generated microbubbles positively. It was experienced that when preparing a production line including pumping the heated protein solution into the mixing device, such as into a colloid mill, the pump generated pressure pulses that widened the size distribution of the microbubbles generated in the mixing device. Hence, in a further embodiment of the invention the process includes a step of feeding the protein solution under a stabile pressure, without generation of any pressure pulses, before this protein solution is heated and mixed with the gas. Such steady feeding pressure is achieved by the use of pressurized feeding tank. More particularly, the process uses a stabile pressure of the protein solution feed stream and this provides a steady flow rate, such as a rate of 0.5-3.0 liters per minute, e.g. 1-2 liters per minute. The flow of the protein solution from the feeding tank and the flow rate of this is controlled and optionally regulated, possibly before the heating starts.

In an embodiment, the process includes all the elements of heating of the gas stream and the protein solution stream, combination of the heated gas and the heated protein solution at the inlet of the mixing device and feeding the protein solution under a stabile pressure.

In the process of an embodiment of the invention, the mixture of the gas and the protein solution is thoroughly mixed by subjecting this to mechanical shear forces. The mechanical shear forces employed prepare microbubbles of the requested size. This is achieved by using a mixing device in which high mechanical shear forces are produced, such as a high speed mixer, a mill, a rotor stator, a fluidizer and the like. In an embodiment of the invention, a mill, such as a colloid mill or a cone mill, is used in step (iv) of dispersinging the protein solution and the gas. Such mill comprises a high-speed rotor and an accompanying stator having opposing faces. Mixers that utilize a rotor and a stationary stator operate at considerably high rotational speeds that produce high rotor tip speeds. The differential speed between the rotor and the stator imparts extremely high shear and turbulent energy in the gap between the rotor and stator. Therefore, the tip speed is a very important factor when considering the amount of shear input into the product. In the process of some embodiments of the invention, the relative speed of the rotor and stator surfaces should be at least 20 m/s. If the rotor is conical, the speed at the surface will depend on the diameter and hence vary over the cone from the tip to the base. Thus the heated mixture of gas and protein solution is passed through a zone in which it is subject to shear forces exerted by surfaces moving relative to each other at a speed of at least 20 m/s, in particular at least 25 m/s or at least 30 m/s, and more particularly, at least 35 m/s. For example, up to 100 m/s, in particular, up to 60 m/s, and more specifically, up to 50 m/s, at the tip.

In one embodiment of the invention, the process includes a further step, after step iv, transferring the prepared composition into bulk containers or directly into a filling tank. The bulk container is e.g. a flexible big bag, e.g. of a volume of 10-100 liters. Before transferring the prepared product, i.e. the composition comprising encapsulated gas microbubbles, from the mixing device to the bulk container or filling tank, the temperature of the composition is reduced, for instance by the use of a heat exchanger. The temperature of the product flow out of the mixing device is e.g. reduced to a temperature of 20-30° C., such as to 25-28° C.

Using the process of some embodiments of the invention, a narrow size distribution of the generated microbubbles is achieved, and the process repeatedly provides a product according to product specifications. This is important in order to provide an economically viable process, particularly as the ingredients used are expensive, and loss of material due to production of micobubbles not meeting the specification requirements are avoided by this process. In addition to the improvements of the claimed process, parameters like the flow of the gas and the flow of the protein solution, and the ratio between these, the temperature of the protein solution and the speed of the mixer (rotor speed) affect the characteristics of the product and needs to be optimised. For any given product, its characteristics are defined clinically. For instance, for Optison™ the mean diameter range is 3.0-4.5 μm wherein 95% are less than 10 μm. The concentration specification is 5.0-8.0×10$^8$ microbubbles/ml. The microbubbles prepared by the process of embodiments of the invention have a narrow size distribution and a well-defined mean particle size having a low standard deviation. The microbubbles produced will have a narrow size distribution about the desired microbubble size, generally 1 to 7 μm, e.g. 3-5 μm, and the standard deviation is small. In a range of examples run, as shown in Example 1, the mean particle size achieved was very stable and varied between 2.8 and 4.3 μm. By using the process of embodiments of the invention, such as when producing microbubbles of human serum albumin and a perfluorinated gas, a standard deviation in particle size of 0.18-0.25 μm was achieved. Given in percentage a standard deviation for the particle size of less than 20%, such as less than 10% is achieved by the process. When preparing particles having a mean particle size within the range of 3.0-4.5 μm a standard deviation of 7.3% or less is achieved. In addition, a well-defined concentration of microbubbles (particles/volume) is achieved having a low standard deviation. A concentration varying from 3.1 to 11.8×10$^8$ microbubbles/ml was achieved, as reported in example 1, with a majority of the runs providing a concentration between 5.0 and 8.0×10$^8$ microbubbles/ml. The standard deviation in concentration is e.g. between 0.40 and 0.70×10$^8$ microbubbles/ml. Given in percentage a standard deviation for the obtained concentration is less than 15% and more particularly less than 12%. Hence, the requirements according to the product specification regarding concentration and particles size are achieved by the claimed process.

The gas microbubbles prepared according to some embodiments of the process of the invention are stabilised by a stabilizing agent which encloses the gas microbubbles, retarding the diffusion of the gas into the surrounding liquid and preventing the fusion between microbubbles. For the process of some embodiments of the invention, such stabilising agent is heat-sensitive so that it can become partially insolubilized by heating during the production process. The material for forming the microbubbles may be an amino acid polymer. Such polymers are biodegradable by proteolytic enzyme action. Usable amino acid polymers include natural amino acids (proteins) and synthetic amino acid polymers. More particularly, the protein is albumin, which may be animal or human albumin, but in particular human serum albumin. Other water soluble proteins such as hemoglobin can be substituted for albumin, more particularly, human hemoglobin. Usable synthetic amino acid polymers include poly-L-lysine and poly-L-glutamic acid. For example, a poly-L-lysine or poly-L-glutamic acid in the molecular weight range of 20,000-50,000 can be used alone or in combination with another polymer such as albumin. Protein derivatives or fractions of proteins are also within the scope of the invention. The actual denaturation temperature is in a range depending on the protein or protein derivatives used.

Biocompatible gases may be employed in the microbubbles of the compositions, it being appreciated that the term "gas", include any substances (including mixtures) substantially or completely in gaseous (including vapour) form at the normal human body temperature of 37° C. The gas may thus, for example, comprise air, nitrogen, oxygen, carbon dioxide, hydrogen, nitrous oxide, an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing.

Compositions may comprise a halogenated low molecular weight hydrocarbon. At least some of the halogen atoms in halogenated gases are fluorine atoms. Thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include fluorinated, e.g. perfluorinated, ketones such as perfluoroacetone and fluorinated, e.g. perfluorinated, ethers such as perfluorodiethyl ether. The process of some embodiments of the invention may be used for compositions comprising fluorinated gases such as sulphur fluorides or fluorocarbons (e.g. perfluorocarbons) which are known to form particularly stable microbubble suspensions. In particular, $SF_6$, perfluoropropane and perfluorobutane may be used and more particularly, perfluoropropane.

The process of some embodiments of the invention may be used for preparation of a composition comprising microbubbles comprising proteins, particularly comprising albumin, encapsulating a perfluorocarbon gas, and more particularly perfluorpropane, also called octafluoropropane (OFP) or perflutren. In an embodiment the product Optison™ is produced according to the claimed process.

In a second aspect the invention provides a composition prepared according to the process of the first aspect. The composition may be for therapeutic or diagnostic purposes, or combined, and is for diagnostic use as an ultrasound contrast media. The composition may be a ready-made preparation, i.e. the composition is a dispersion of gas microbubbles in a physiologically acceptable aqueous carrier, such as in water for injection. After filling into smaller containers, such as into vials or bottles, and capping, re-suspension by gentle shaking may be needed to provide a homogeneous suspension before injecting to a patient. The composition is hence ready for being injected into a patient, being a human being or animal. Ultrasound contrast media wherein the microbubble comprises a vector having affinity for a biological target are also enclosed. A variety of imaging techniques may be employed in ultrasound applications, for example including fundamental and harmonic B-mode imaging and fundamental and harmonic Doppler imaging; if desired three-dimensional imaging techniques may be used.

In a third aspect, the invention provides a feeding pipe useful in the preparation of a composition comprising encapsulated gas microbubbles, wherein the feeding pipe comprises i) a first inlet and a second inlet providing the respective openings of two paths,
ii) a heat transferring section comprising a longitudinal wall separating the two paths,
iii) one outlet connectable to an inlet of a mixing device.

The two inlets are designed to connect with transfer lines or tubes, e.g. by using clamps, such as tree clamps, providing leak proof connections. One inlet may be connectable with a tube transporting a liquid composition, such as an aqueous solution of a heat-denaturable protein, and the other inlet is connectable with a tube transporting a gas, such as a perfluorocarbon gas. The two inlets are separated, providing openings of two pipe sections that are combined, seen from the outside, at the start of the heat transferring section.

The heat transferring section may makes up a predominant part of the pipe wherein the two paths go in parallel and heat can be transferred from a stream transported in one path to the stream of the other path. The pipe may have, at least in the heat transferring section, an outer cylindrical surface providing two separated paths in one cylindrical pipe, wherein the paths are separated by a longitudinal inner wall preventing mixture of the streams running in the paths. In one embodiment, the interior cylindrical volume is split in two halfs by the longitudinal wall providing two half pipes, one for each path. In another embodiment, the two paths are separated by having one inner pipe running within the outer pipe. Hence, in this embodiment the longitudinal wall makes up a cylindrical inner pipe such that one path runs within the other path, wherein the two pipes have the same centre line. More particularly, the gas stream runs in the inner path and the liquid composition runs in the outer path. When there is a temperature difference between the streams in the two paths, this difference will diminish as the streams move in parallel towards the outlet. The length of the pipe should be long enough to enable sufficient heat transfer from the stream of one path to the other. The length of the heat transferring section is sufficiently long to assure the desired heat exchange and is e.g. 10-100 cm, such as 15-50 cm, and in particular 20-40 cm. An appropriate inner diameter size for the inlet for the liquid composition is 5-40 mm, such as 15-25 mm. An appropriate diameter size for the inlet for the gas is 0.5-40 mm. In the embodiment wherein the pipe is split in two half pipes the gas inlet may have the same dimensions as the inlet for the protein solution. In the embodiment wherein the gas stream runs in an inner pipe, the diameter of the gas pipe is considerably less than the diameter of the pipe for the protein solution, e.g. only 0.5-3.0 mm. For the heat transferring section, the outer diameter may be about the same as the outer diameter of the first pipe section for the protein solution, e.g. 10-45 mm.

The outlet of the feeding pipe is connectable with an inlet of a mixing device, using for instance a clamp, such as a tree clamp, providing a leak proof connection. At, or near, the outlet of the pipe the longitudinal inner wall ends and the two paths of the pipe are combined such that the streams running in these will mix providing a uniform composition which is continuously the same throughout the process. Accordingly, when the feeding pipe is connected to a mixing device either a newly mixed composition will enter this or the liquid composition and the gas will mix at the inlet or right after entering this. In the embodiment wherein the gas runs in an inner pipe, this pipe may end, and have the outlet, at the same place as the outlet of the protein solution. Hence, the inner and outer pipe then have the same length. Alternatively, the inner pipe may end slightly before the outlet of the outer pipe, ensuring that the two components are mixed before entering the mixing device. Yet in another alternative the inner pipe may be longer than the outer pipe and extend outside the outlet of the outer pipe. In this alternative, when the feeding pipe is coupled to the mixing device, the inner pipe will extend into the mixing device. In the embodiment wherein the heat transferring section of the pipe is split in two half pipes by a longitudinal wall this wall may end at the outlet of the pipe or alternatively slightly before the outlet, ensuring that the components are mixed before entering the mixing device.

The feeding pipe may be of any convenient material or combination of materials but will desirably be of metal or ceramic, in particular of a metal such as steel, and in particular stainless steel.

In another aspect, the invention provides an apparatus for preparation of a composition comprising encapsulated gas microbubbles, the apparatus comprises a feeding pipe as described in the third aspect of the invention.

The apparatus of the invention hence comprises
i) a mixing device generating high mechanical shear forces, and having an inlet and an outlet;
ii) a feeding pipe comprising a first inlet and a second inlet providing the respective openings of two paths, a heat transferring section comprising a longitudinal wall separating the two paths, and one outlet connected to the inlet of the mixing device;
iii) a feeding tank for liquid composition connected to the first inlet of the feeding pipe;
iv) a gas tank connected to the second inlet of the feeding pipe.

The mixing device is a device in which high mechanical shear forces are produced, such as a high speed mixer, a mill, a rotor stator, a fluidizer or the like. In an embodiment of the invention the mixing device is a mill, such as a colloid mill or a cone mill, and this is used in the dispersing of the protein solution and the gas. Such mill comprises a high-speed rotor and an accompanying stator having opposing faces, i.e. a mixer in which the starting mixture is passed through a zone in which shear forces are exerted upon it by relative rotation of two surfaces, one on an element referred to as a rotor and the other on an element referred to as a stator. Mixers that utilize a rotor and a stationary stator operate at considerably high rotational speeds that produce high rotor tip speeds. The differential speed between the rotor and the stator imparts extremely high shear and turbulent energy in the gap between the rotor and stator. In the mixing device of an embodiment of the apparatus of the invention, the surfaces moving relatively to each other to create the shear force zones are desirably separated from each other by less than 2 mm, less than 1 mm, and in particular, less than 600 µm, e.g. 300 to 500 µm. The distance between the rotor and the stator may be adjustable, e.g. between 0.2-0.6 mm. The optimum separation will depend upon the viscosity of the mixture passing through the shear force zones and the minimum separation may be imposed by manufacturing constraints. The protein solution/gas mixture is dispersed and cavitates between the surfaces of the rotor and stator. The mixing device further comprises a mixing chamber disposed with a rotor and drive means therefor, including a motor and bearings. The mixer has in facing relationship to the rotor a stator, the stator and rotor may have smooth surfaces or may in one embodiment have axially extending interlocking ridges and grooves provided with radially extending fluid transit means whereby to define a plurality of shear force zones for fluid passing radially between the rotor and the stator from the inlet. In an embodiment of the mixer apparatus of the invention, the inlet is located radially inwardly of the shear force zones, and more particularly, at or near the rotation axis of the rotor. Desirably the inlet of the mixing device is adjacent the drive shaft for the rotor, so that the gas and protein solution mixture from the feeding pipe outlet may be further pre-mixed if needed in the premixing chamber before entering the shear force zones.

To ensure that adequate mixing occurs, a second rotor, and if desired further rotors, for example up to 5 rotors, may be provided, driven by the same drive means, more particularly a rotating drive shaft. Where a second rotor is provided, the mixer will desirably have a second mixing chamber having an inlet port communicating with the outlet port of the first chamber and having its own outlet port.

The rotors and stators may be of any convenient material or combination of materials but will desirably be of metal or ceramic, in particular of a metal such as steel. Moreover, the rotor and stator surfaces may if desired be coated or treated to provide optimum yield or characteristics for the end product. The dimensions of the rotor and stator components will depend upon the material from which the rotor is made, the intended vesicle upper size limits, rotation speeds, rotor diameters, and mixture viscosities, but generally for stainless steel components, rotation speeds of 5000 to 12000 rpm, and aqueous mixtures, rotor diameters of up to 25 cm, e.g. 7.5 to 15 cm, may be used. These parameters however are not limiting and mixing devices useful in the apparatus of the invention may be produced with other dimensions, materials and operating speeds.

As the mixing device of the apparatus of the invention can generate a noticeable heating effect and as microbubble size and stability may be affected by temperature, it is particularly desirable to provide the mixing device with temperature control means, for example thermostat-controlled heating or cooling means such as a cooling jacket surrounding the mixing chamber or alternatively a cooling element such as heat exchanger within or in thermal connection with the stator or the rotor, or alternatively or additionally a cooling element within or in thermal connection with the rotor drive shaft or the mechanical seal surrounding the rotor drive shaft. The temperature of the mixture may be monitored at the outlet of each mixing chamber or at the rim of the rotor and this may be used to control such temperature control means. It is further desirable to provide the mixing device with a cooling element, such as a heat exchanger, in thermal connection with the product stream from the outlet of the mixing device, to reduce the temperature of the product stream product flow out of the mixing device e.g. to a temperature of 20-30° C., such as to 25-28° C. The outlet may be positioned towards the bottom of the mill.

The feeding pipe of the apparatus is described in the third aspect.

The apparatus further includes a feeding tank for a liquid composition, such as a protein solution, connected to the first inlet of the feeding pipe, via other entities as described below. The feeding tank is a pressurized feeding tank providing a steady feeding pressure, and this has been found to affect the size distribution of the generated microbubbles positively, providing a narrow size distribution. The feeding tank is pressurized e.g. by blowing an inert gas such as compressed air or nitrogen gas into the feeding tank. More particularly, this gas is added through a sterile filter. The pressure in the feeding tank is e.g. 0.5-3.0 barG (equals 1.5-4.0 barA) and is in particular 1-2 barG. Such pressurized feeding tank may further include mixing means, such as a stirrer, providing a homogeneous solution to be heated and delivered into the mixing device. The feeding tank is e.g. 10-200 liters, such as 50-150 liters, and provides a steady flow rate, such as a rate of 0.5-3.0 liters per minute, e.g. 1-2 liters per minute. The flow of the protein solution from the feeding tank and the flow rate of this is controlled and optionally regulated, before the heating starts. This can be done by including a flow controller and a regulating valve at the outlet of the feeding tank. Further, between the feeding tank and the feeding pipe the protein solution feed stream is heated to a temperature necessary to achieve incipient denaturation of the protein. It is desirable to provide the feed stream with temperature control means, for example thermostat-controlled heating such as by a heat exchanger within or in thermal connection with the feed stream. The temperature of the protein solution feed stream may be monitored before entering into the feeding pipe, wherein heat will be transferred from the protein solution feed stream to the gas.

The apparatus further includes a gas tank connected to the second inlet of the feeding pipe, via other entities as described below. The gas tank is the source of the gas to be encapsulated in the microbubbles. The gas flow rate of this is controlled and optionally regulated, before the gas enters the feeding pipe wherein it is heated. This regulation can be done by including a flow controller and a regulating valve at the outlet of the gas tank. The gas tank provides the gas under pressure, e.g. under a pressure of 1-4 barG. The gas flow rate is e.g. 0.5-2.5 liters/minute. However, the pressure of the gas into the mill is set by the number of revolutions per minute and of the flow rate, and cannot be regulated easily by the gas.

One or more sterile filters may be included in the apparatus to eliminate or kill all forms of microbial life, including transmissible agents.

Some embodiments of the invention will now be described by way of example only and with reference to the accompanying drawings, in which FIG. 1 schematically shows an apparatus according to an embodiment of the invention and which is useful in the preparation of a composition comprising gas microbubbles encapsulated by a denatured protein. Hence, FIG. 1 shows an apparatus 1 wherein the main components are a mixing device 20, a feeding pipe 30, a feeding tank 40 for liquid composition and a gas tank 50. The feeding tank 40 comprises a liquid solution 42, such as e.g. a denaturable serum albumin solution. Into the feeding tank 40 are the components 41, making up the solution, being fed. In a particular embodiment, such components are serum albumin 41a, e.g. provided in a 5% solution, water for injection 41b and NaCl 41c, more particularly in a 0.9% solution, making a 1% human serum albumin solution 42. Compressed air, or nitrogen gas, is blown into the feeding tank 40 through a sterile filter 44, to pressurize the content. Further, a temperature control unit 47 is connected to the feeding tank 40. To provide a homogeneous solution 42 a stirrer 46 is further included in the feeding tank 40. The flow of the protein solution from the feeding tank 40 is controlled and optionally regulated by a flow controller 62 and a regulating valve 64 near by the outlet of the feeding tank 40. The solution is then run through a sterile filter 66. Further, between the feeding tank 40 and the feeding pipe 30 the stream of protein solution 42 is heated to a temperature necessary to achieve incipient denaturation of the protein using a heat exchanger 68. After having been heated to the desired temperature the protein solution enters the feeding pipe 30, through an inlet 32.

The gas tank 50 provides the gas 52 to be encapsulated in the microbubbles. The flow of the gas from the gas tank 50 is controlled and optionally regulated by a flow controller 72 and a regulating valve 74 near by the outlet of the gas tank 50. Before entering the feeding pipe 30 the gas 52 runs through a sterile filter 76. The gas then enters the feeding pipe 30 through an inlet 34, separated from the inlet 32 for the protein solution. In the feeding pipe 30 there will be a temperature transfer from the protein solution to the gas, ensuring that the gas does not expand of any significance when entering the mixing device 20. The protein solution 42 and the gas 52 flow out of an outlet 36 of the pipe 30 and into the mixing device 20 through an inlet 24, as a mixed composition. The outlet 36 of the feeding pipe 30 and the inlet 24 of the mixing device 20 may be connected e.g. by a clamp. The mixing device 20 comprises a mill 22 comprising a rotor 25 and a stator 26, wherein the rotor 25 is driven by a motor 29 and drive means therefor, including bearings 28 and optional cooling systems 27. The generated product 80, i.e. a composition of gas microbubbles encapsulated by denatured protein, is withdrawn from the mixing device at the bottom of the mill 22. The temperature of the product stream 80 is optionally measured and regulated using a temperature control unit 82, e.g. comprising a heat exchanger.

Figure 2A:
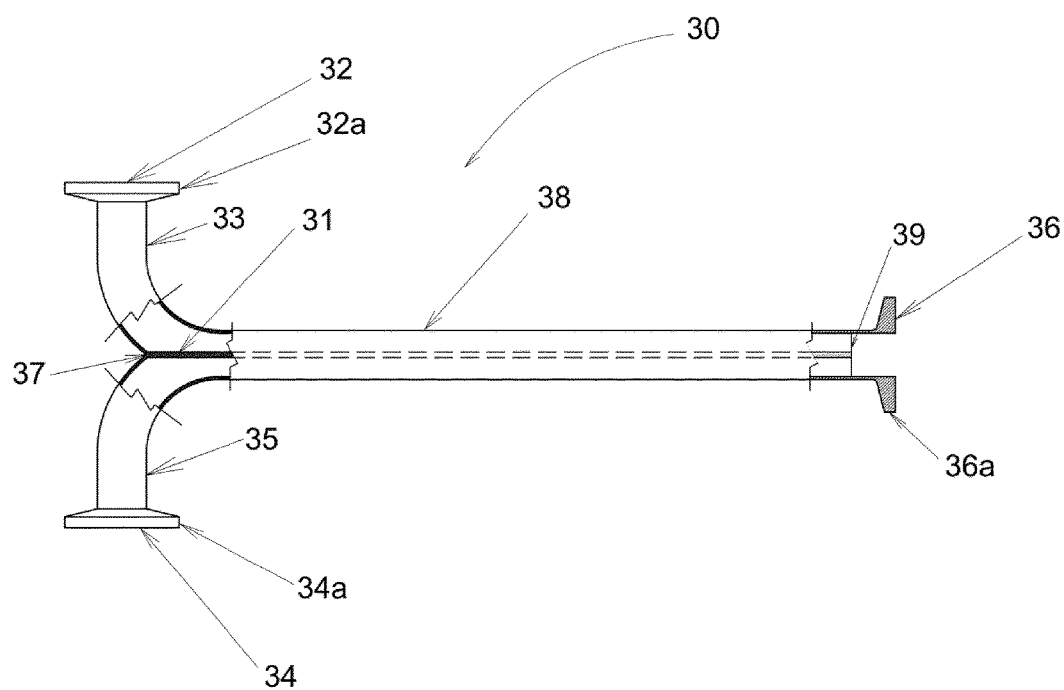
FIGS. 2A, 2B, and 2C schematically show a feeding pipe according to an embodiment of the invention comprising two paths, one for transporting gas and one for the protein solution.
Figure 2B:
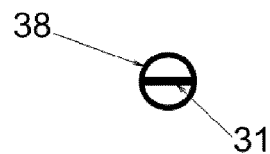
Figure 2C:
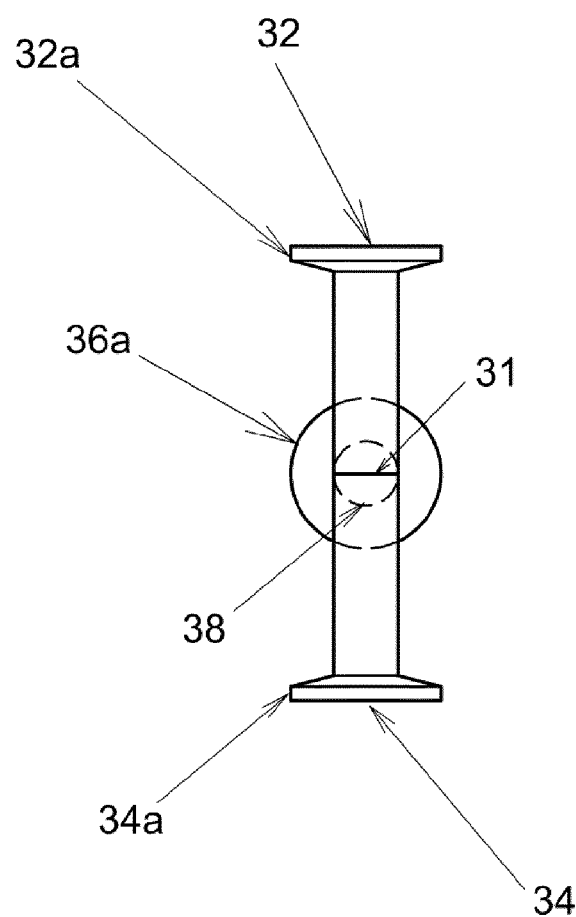

FIGS. 2 and 3 show alternative feeding pipes according to some embodiments of the invention. FIG. 2A shows a feeding pipe 30 having a first inlet 32 providing the opening to a first pipe section 33. The inlet 32, which is for feeding a protein solution, has a circumference 32a connectable with a tube or transfer line using a clamp. A second inlet 34, with a circumference 34a, provides the opening to a second pipe section 35 for feeding a gas. The pipe sections 34 and 35 are merged, seen from the outside, at a combination point 37, providing one pipe with an outer cylindrical wall 38 and an inner longitudinal wall 31 separating the two streams. The section of the pipe 30 from the combination point 37 to the end of the longitudinal wall 31 near the outlet 36 provides the heat transferring section. As shown, the longitudinal wall 31 ends slightly before the outlet 36. In other embodiments the wall may end closer to or at the outlet 36. The outlet 36 of the pipe 30 has a circumference 36a connectable with an inlet of a mixing device using e.g. a clamp. FIG. 2B shows the cross section of the heat transferring section of the pipe 30 having a longitudinal wall 31 and an outer cylindrical wall 38. FIG. 2C shows the pipe 30 from a side view seen from the outlet 36, having a first inlet 32 with a circumference 32a and a second inlet 34 with a circumference 34a, and having an outer cylindrical wall 38.

Figure 3A:
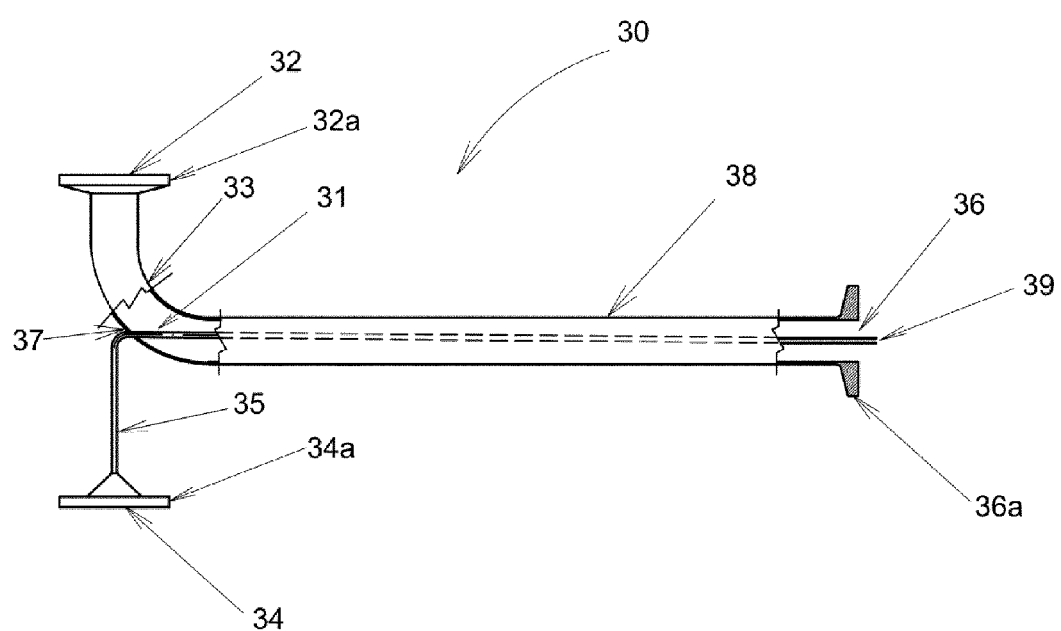
FIGS. 3A, 3B, and 3C schematically show an alternative feeding pipe according to an embodiment of the invention.
Figure 3B:
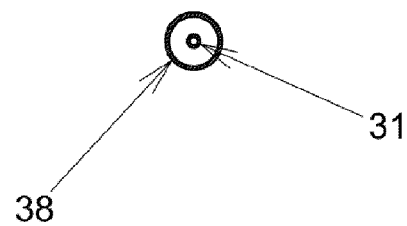
Figure 3C:
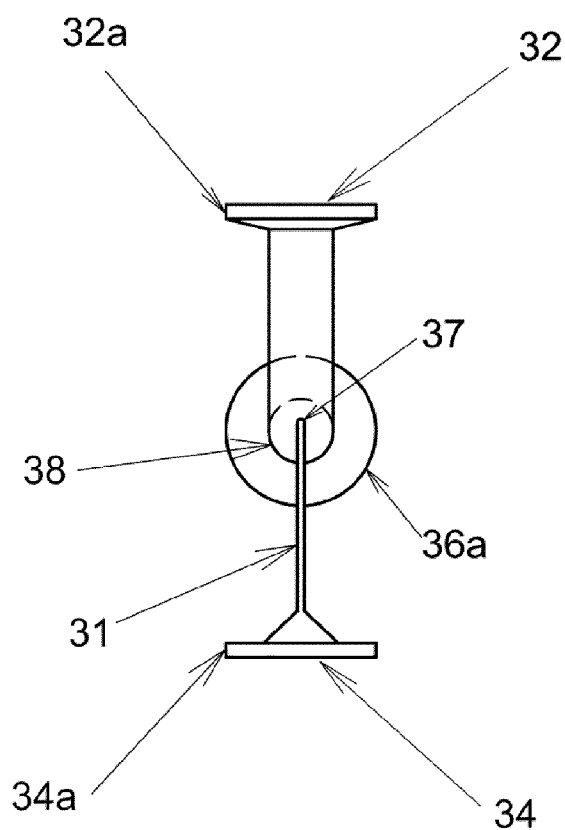

FIG. 3 shows an alternative feeding pipe, wherein FIG. 3a shows the feeding pipe 30 having a first inlet 32 providing the opening to a first pipe section 33. The inlet 32, which is for feeding a protein solution, has a circumference 32a. A second inlet 34, with a circumference 34a, provides the opening to a second pipe section 35 for feeding a gas. The pipe sections 33 and 35 are merged, seen from the outside, at a combination point 37, providing one pipe with an outer cylindrical wall 38 and running within this an inner pipe 31 for the gas feed. The section of the pipe 30 from the combination point 37 to the outlet 36 provides the heat transferring section. As shown, the inner pipe 31 ends slightly outside the outlet 36, having an outlet 39. In other embodiments the pipe may end closer to or at the outlet or slightly before the outlet 36. The outlet 36 of the pipe 30 has a circumference 36a connectable with an inlet of a mixing device using e.g. a clamp. FIG. 3b shows the cross section of the heat transferring section of the pipe 30 having an inner pipe 31 and an outer cylindrical wall 38. FIG. 3c shows the pipe 30 seen from the outlet 36, having a first inlet 32 with a circumference 32a and a second inlet 34 with a circumference 34a, and having an outer cylindrical wall 38.

Embodiments of the invention are now illustrated with reference to the following non-limiting examples.

EXAMPLES

Example 1: Preparation of Optison™

Optison™ batches manufactured according to an embodiment of the process of the invention, have been evaluated and compared with respect to variability and predictability with a process of a third party. The purpose was to compare the predictability of two manufacturing methods in order to understand the future predictability of product quality.

25 experiments preparing batches of Optison™ were manufactured by GE Healthcare according to the claimed process, and 19 experiments preparing batches of Optison™ manufactured by a third party process, have been evaluated and compared with respect to variability and predictability.

The GE process included use of an apparatus as shown in FIG. 1 including a feeding pipe wherein heat is transferred from the protein solution (human serum albumin) to the gas (perfluoropropane=OFP) and wherein the protein solution and the gas are mixed right before the dispersing step, using a mill. A pressurized feeding tank was used for delivery of the protein solution to the mill.

The process of the third party included an apparatus wherein a heated protein solution (human serum albumin) was mixed with an unheated gas (OFP) at a distance of about 1 meter prior to entering the mill. A peristaltic pump was used for delivery of the protein solution to the mill.

The raw data is given in Table 1 and 2, providing the parameters used in the two processes. The mean particle sizes and the concentrations obtained were identified.

TABLE 1

Data from third party process-for comparison

| Run Order | Mill Speed (RPM) | Albumin Flow (cc/min.) | OFP Gas Flow (cc/min.) | Albumin Temp. (° C.) | MPS [μm] | Conc. [×10$^8$ microbubbles/ml] |
|---|---|---|---|---|---|---|
| 1 | 11500 | 1000 | 950 | 67 | 5.21 | 14.44 |
| 2 | 9000 | 2000 | 950 | 67 | 4.3 | 4.1 |
| 3 | 10250 | 1500 | 800 | 70 | 4.496 | 9.278 |
| 4 | 9000 | 2000 | 650 | 67 | 3.8 | 3.8 |
| 5 | 11500 | 2000 | 950 | 73 | 3.548 | 14.79 |
| 6 | 9000 | 1000 | 950 | 73 | 6.504 | 4.545 |
| 7 | 9000 | 2000 | 950 | 73 | 5.9 | 3.3 |
| 8 | 9000 | 1000 | 650 | 73 | 6.9 | 5.8 |
| 9 | 10250 | 1500 | 800 | 70 | 4.586 | 9.143 |
| 10 | 11500 | 2000 | 950 | 67 | 3.022 | 14.1 |
| 11 | 10250 | 1500 | 800 | 70 | 4.7 | 9.3 |
| 12 | 9000 | 1000 | 650 | 67 | 6.2 | 5.5 |
| 13 | 11500 | 2000 | 650 | 73 | 3.135 | 16.63 |
| 14 | 11500 | 1000 | 950 | 73 | 5.363 | 14.09 |
| 15 | 11500 | 1000 | 650 | 73 | 4.321 | 19.83 |
| 16 | 9000 | 1000 | 950 | 67 | 7.074 | 4.553 |
| 17 | 11500 | 1000 | 650 | 67 | 4.1 | 21 |
| 18 | 11500 | 2000 | 650 | 67 | 2.7 | 15.92 |
| 19 | 9000 | 2000 | 650 | 73 | 4.7 | 3.5 |

TABLE 2

Data from GE process

| Run Order | Mill Speed (RPM) | Albumin Flow (cc/min.) | OFP Gas Flow (cc/min.) | Albumin Temp. (° C.) | MPS [μm] | Conc. [×10$^8$ microbubbles/ml] |
|---|---|---|---|---|---|---|
| 1 | 10250 | 1500 | 800 | 69 | 3.99 | 11.7 |
| 2 | 9300 | 1800 | 840 | 66 | 3.83 | 6.93 |
| 3 | 8800 | 1500 | 940 | 69 | 3.99 | 6.3 |
| 4 | 9800 | 2100 | 940 | 68 | 3.38 | 7.45 |
| 5 | 9300 | 1800 | 840 | 66.5 | 3.86 | 5.97 |
| 6 | 8800 | 1500 | 740 | 66.5 | 3.97 | 5.09 |
| 7 | 9800 | 2100 | 740 | 64.5 | 3.51 | 6.73 |
| 8 | 8800 | 2100 | 940 | 64.5 | 3.67 | 4.21 |
| 9 | 8800 | 2100 | 740 | 67.5 | 4.19 | 3.57 |
| 10 | 9800 | 1500 | 940 | 64.5 | 3.42 | 9.39 |
| 11 | 9300 | 1800 | 840 | 67 | 3.69 | 7.36 |
| 12 | 9300 | 1800 | 840 | 67 | 3.59 | 7.16 |
| 13 | 9300 | 1800 | 840 | 66 | 3.43 | 6.93 |
| 14 | 9300 | 1800 | 840 | 66 | 3.5 | 6.68 |
| 15 | 8500 | 1000 | 950 | 68 | 3.89 | 8.04 |
| 16 | 8500 | 1000 | 950 | 68 | 3.81 | 8.3 |
| 17 | 8000 | 1300 | 1150 | 70.6 | 2.78 | 3.4 |
| 18 | 8500 | 1000 | 950 | 68.1 | 3.75 | 6.85 |
| 19 | 9000 | 700 | 750 | 66.3 | 3.76 | 9.6 |
| 20 | 8000 | 1300 | 750 | 65.7 | 3.58 | 3.1 |
| 21 | 8000 | 700 | 1150 | 66.4 | 3.08 | 7.7 |
| 22 | 9000 | 1200 | 750 | 72 | 4.27 | 7.57 |
| 23 | 9000 | 1200 | 750 | 70 | 4.19 | 7.25 |
| 24 | 9000 | 1400 | 750 | 70 | 4.268 | 6.62 |

The standard deviations (SD) (~root mean square error of calibration RMSEC) for the particle size obtained and for the concentration were found:
Third party process:
a. Mean particle size: SD of 0.33 μm
b. Concentration: SD of 1.19×10$^8$ microbubbles/ml
Claimed process:
a. Particle size: SD of 0.22 μm
b. Concentration: SD of 0.55×10$^8$ microbubbles/ml The standard deviations indicate an increased manufacturing reproducibility, and hence an increased predictability of product quality, by applying embodiments of the new and improved process of the invention.

It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details. Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

The invention claimed is:

1. A process for preparing a composition comprising encapsulated gas microbubbles, the process comprising:
   i) heating an aqueous protein solution of a heat-denaturable protein to form a heated protein solution at a temperature necessary to achieve incipient denaturation;
   ii) heating a gas by using heat from the heated protein solution by transferring the gas and the heated protein solution via separate and adjacent flow paths, wherein a longitudinal wall separates the flow paths prior to combining the gas and the heated protein solution;
   iii) mixing the heated gas and the heated protein solution to obtain a gas/liquid mixture; and
   iv) subjecting the gas/liquid mixture to mechanical shear forces to form a composition of gas microbubbles encapsulated by denatured protein;
   wherein the gas is characterized as being in a gaseous form at 37 degrees Celsius and is not mixed with any substances prior to step (iii).

2. The process as claimed in claim 1, wherein the aqueous solution of the heat-denaturable protein is heated to a temperature of 50-100° C.

3. The process as claimed in claim 1, wherein the gas is heated to a temperature close to the temperature of the heated protein solution.

4. The process as claimed in claim 1, wherein the aqueous protein solution is heated in step (i) under a steady feeding pressure.

5. The process as claimed in claim 1, wherein the microbubbles have a particle size with a standard deviation less than 20% of the mean particle size.

6. The process as claimed in claim 1, wherein the protein is human serum albumin.

7. The process as claimed in claim 3, wherein the gas is heated to at least a temperature of the denaturation of the protein minus 20° C.

8. The process as claimed in claim 2, wherein the gas is heated to a temperature close to the temperature of the heated protein solution.

9. The process as claimed in claim 8, wherein the gas is heated to at least a temperature of the denaturation of the protein minus 20° C.

10. The process as claimed in claim 2, wherein the aqueous protein solution is heated in step (i) under a steady feeding pressure.

11. The process as claimed in claim 3, wherein the aqueous protein solution is heated in step (i) under a steady feeding pressure.

* * * * *